United States Patent
Foelling (10) Patent No.: US 10,234,672 B2
(45) Date of Patent: Mar. 19, 2019

(54) LIGHT-MICROSCOPIC METHOD OF LOCALIZATION MICROSCOPY FOR LOCALIZING POINT OBJECTS

(71) Applicant: LEICA MICROSYSTEMS CMS GMBH, Wetzlar (DE)

(72) Inventor: Jonas Foelling, Heidelberg (DE)

(73) Assignee: LEICA MICROSYSTEMS CMS GMBH, Wetzlar (DE)

( * ) Notice: Subject to any disclaimer, the term of this patent is extended or adjusted under 35 U.S.C. 154(b) by 323 days.

(21) Appl. No.: 14/901,740

(22) PCT Filed: Jul. 1, 2014

(86) PCT No.: PCT/EP2014/063918
§ 371 (c)(1),
(2) Date: Dec. 29, 2015

(87) PCT Pub. No.: WO2015/000877
PCT Pub. Date: Jan. 8, 2015

(65) Prior Publication Data
US 2016/0370570 A1 Dec. 22, 2016

(30) Foreign Application Priority Data

Jul. 1, 2013 (DE) .................. 10 2013 106 895

(51) Int. Cl.
*G02B 21/36* (2006.01)
*G02B 27/00* (2006.01)
(Continued)

(52) U.S. Cl.
CPC ....... *G02B 21/367* (2013.01); *G01N 21/6458* (2013.01); *G02B 21/16* (2013.01); *G02B 27/0025* (2013.01); *G02B 27/58* (2013.01)

(58) Field of Classification Search
CPC .. G02B 21/367; G02B 21/16; G02B 27/0025; G02B 27/58; G01N 21/6458
See application file for complete search history.

(56) References Cited

U.S. PATENT DOCUMENTS 5,491,550 A 2/1996 Dabbs
7,639,419 B2 * 12/2009 Chuang .............. G01N 21/8806
359/355

(Continued)

FOREIGN PATENT DOCUMENTS

DE 154643 A1 4/1982
DE 261224 A1 10/1988
(Continued)

OTHER PUBLICATIONS

Laurent Holtzer, et al., "Nanometric three-dimensional tracking of individual quantum dots in cells", Applied Physics Letters 90, Feb. 1, 2007, pp. 053902-1-053902-3.

(Continued)

*Primary Examiner* — Nhon T Diep
(74) *Attorney, Agent, or Firm* — Leydig, Voit & Mayer, Ltd.

(57) ABSTRACT

A light-microscopic method of localization microscopy for localizing point objects in a sample arranged in an object space includes imaging, by an imaging optical unit having a depth of field range of predetermined axial z-extension along its optical axis in the object space, the sample onto a detector; localizing the point objects in the sample within the depth of field range in that, on the basis of a sample image, lateral x/y-positions of the point objects in a direction perpendicular to the optical axis are ascertained; displacing, in the object space relative to the sample the depth of field range within which the point objects are localized in the object space relative to the sample along the optical axis at least once by a predetermined axial z-travel distance; and (Continued)

imaging, by the imaging optical unit in the event of an axially displaced depth of field range.

16 Claims, 5 Drawing Sheets

(51) Int. Cl.
*G01N 21/64* (2006.01)
*G02B 21/16* (2006.01)
*G02B 27/58* (2006.01)

(56) References Cited

U.S. PATENT DOCUMENTS

| | | | |
|---|---|---|---|
| 7,675,045 | B1 | 3/2010 | Werner et al. |
| 9,179,131 | B2* | 11/2015 | Foelling ............ H04N 13/0257 |
| 9,201,011 | B2 | 12/2015 | Kalkbrenner et al. |
| 2001/0040096 | A1 | 11/2001 | Yamamoto et al. |
| 2002/0020800 | A1 | 2/2002 | Knebel et al. |
| 2007/0146873 | A1* | 6/2007 | Ortyn ................. G01N 21/6458 359/386 |
| 2007/0190566 | A1 | 8/2007 | Ontagu |
| 2009/0134342 | A1 | 5/2009 | Hell et al. |
| 2009/0237501 | A1 | 9/2009 | Lemmer et al. |
| 2009/0242798 | A1 | 10/2009 | Bewersdorf et al. |
| 2010/0278400 | A1 | 11/2010 | Piestun et al. |
| 2010/0283835 | A1 | 11/2010 | Bewersdorf et al. |
| 2011/0002530 | A1* | 1/2011 | Zhuang ............. G01N 21/6428 382/154 |
| 2011/0160083 | A1 | 6/2011 | Hell et al. |
| 2011/0249866 | A1 | 10/2011 | Piestun et al. |
| 2012/0224034 | A1 | 9/2012 | Kalkbrenner et al. |
| 2013/0120539 | A1 | 5/2013 | Foelling |
| 2013/0128025 | A1 | 5/2013 | Dyba et al. |
| 2013/0222568 | A1 | 8/2013 | Dyba et al. |
| 2015/0002632 | A1 | 1/2015 | Kalkbrenner et al. |
| 2015/0160446 | A1 | 6/2015 | Kalkbrenner et al. |
| 2015/0309294 | A1 | 10/2015 | Stelzer |

FOREIGN PATENT DOCUMENTS

| | | |
|---|---|---|
| DE | 69115914 T2 | 5/1996 |
| DE | 10039520 A1 | 2/2002 |
| DE | 10257423 A1 | 6/2004 |
| DE | 102006021317 B3 | 10/2007 |
| DE | 60132656 T2 | 5/2008 |
| DE | 102008024568 A1 | 12/2009 |
| DE | 102009043744 A1 | 3/2011 |
| DE | 102010017630 A1 | 12/2011 |
| DE | 102010036709 A1 | 2/2012 |
| DE | 102010044013 A1 | 5/2012 |
| DE | 102011055294 A1 | 5/2013 |
| DE | 102012200344 A1 | 7/2013 |
| DE | 102012201003 A1 | 7/2013 |
| EP | 0244640 B1 | 11/1987 |
| EP | 2592461 A2 | 5/2013 |
| JP | 2001324474 A | 11/2001 |
| JP | 2007199511 A | 8/2007 |
| JP | 2011508214 A | 3/2011 |
| JP | 2011514532 A | 5/2011 |
| WO | WO 9623240 A1 | 8/1996 |
| WO | WO 2006127692 A2 | 11/2006 |
| WO | WO 2007128434 A1 | 11/2007 |
| WO | WO 2008091296 A3 | 7/2008 |
| WO | WO 2009085218 A1 | 7/2009 |
| WO | WO 2009115244 A1 | 9/2009 |

OTHER PUBLICATIONS

H. Pin Kao, et al., "Tracking of Single Fluorescent Particles in Three Dimensions: Use of Cylindrical Optics to Encode Particle Position", Biophysical Journal, vol. 67, Sep. 1994, pp. 1291-1300.

Manuel F. Juette, et al., "Three-dimensional sub-100 nm resolution fluorescence microscopy of thick samples", Nature Methods 5, May 11, 2008, pp. 527-529.

Erdal Toprak, et al., "Three-Dimensional Particle Tracking via Biofocal Imaging", Nano Letters, vol. 7, No. 7, Apr. 18, 2007, pp. 2043-2045.

Sri Rama Prasanna Pavani, et al., "Three-dimensional, single-molecule fluorescence imaging beyond the diffraction limit by using a double-helix point spread function", Proceedings of the National Academy of Sciences of the United States of America, vol. 106, No. 9, Mar. 3, 2009, pp. 2995-2999.

C. Geisler, et al., "Resolution of λ/10 in fluourescence microscopy using fast single molecule photo-switching", Appl. Phys. A 88, Jun. 1, 2007, pp. 223-226.

Bo Huang, et al., Three-Dimensional Super-Resolution Imaging by Stochastic Optical Reconstruction Microscopy, Science, vol. 319, Feb. 8, 2008, pp. 810-819.

Michael j. Rust, et al., Sub-diffraction-limit imaging by stochastic optical reconstruction micrscopy (STORM), Nature Methods 3, Aug. 9, 2006, pp. 793-796.

* cited by examiner

FIG. 6
Step 1

FIG. 7
Step 2

FIG. 8
Step 3

FIG. 9
Step 4

FIG. 10
Step 5

FIG. 11

FIG. 12

LIGHT-MICROSCOPIC METHOD OF LOCALIZATION MICROSCOPY FOR LOCALIZING POINT OBJECTS

CROSS REFERENCE TO RELATED APPLICATIONS

This application is a U.S. National Stage Application under 35 U.S.C. § 371 of International Application No. PCT/EP2014/063918 filed on Jul. 1, 2014, and claims benefit to German Patent Application No. DE 10 2013 106 895.2 filed on Jul. 1, 2013. The International Application was published in German on Jan. 8, 2015 as WO 2015/000877 A1 under PCT Article 21(2).

FIELD

The invention relates to a light-microscopic method for localizing point objects in a sample arranged in an object space and imaged onto a detector by means of an imaging optical unit.

BACKGROUND

Recently, light-microscopic imaging methods have been developed, by means of which sample structures which are smaller than the diffraction-dependent resolution limit of conventional light microscopes can be represented, on the basis of sequential, stochastic localization of individual markers, in particular fluorescent molecules. Such methods are described for example in WO 2006/127692 A2; DE 10 2006 021 317 B3; WO 2007/128434 A1, US 2009/0134342 A1; DE 10 2008 024 568 A1; WO 2008/091296 A2; "Sub-diffraction-limit imaging by stochastic optical reconstruction microscopy (STORM)", Nature Methods 3, 793-796 (2006), M. J. Rust, M. Bates, X. Zhuang; "Resolution of Lambda/10 in fluorescence microscopy using fast single molecule photo-switching", Geisler C. et al, Appl. Phys. A, 88, 223-226 (2007). This new branch of microscopy is also referred to as localization microscopy. The methods used are known in the literature for example by the names (F)PALM ((fluorescence) photoactivation localization microscopy), PALMIRA (PALM with independently running acquisition), GSD(IM) (ground state depletion individual molecule return) microscopy or (F)STORM ((fluorescence) stochastic optical reconstruction microscopy).

What the new methods have in common is that the sample structures to be imaged are prepared using point objects, referred to as markers, which have two distinguishable states, namely a "bright" state and a "dark" state. If for example fluorescent dyes are used as markers, the bright state is a state capable of fluorescence and the dark state is a state incapable of fluorescence. In preferred embodiments, as in WO 2008/091296 A2 and WO 2006/127692 A2 for example, photoswitchable or photoactivatable fluorescent molecules are used. Alternatively, as in DE 10 2006 021 317 B3 for example, inherent dark states of standard fluorescent molecules can be used.

In order to image sample structures at a resolution which is higher than the conventional resolution limit of the imaging optical unit, now a small subset of the markers is repeatedly converted into the bright state. In so doing, in the simplest case the density of the markers forming this active subset is to be selected such that the average distance between adjacent markers in the bright, and therefore light-microscopically imageable, state is greater than the resolution limit of the imaging optical unit. The markers forming the active subset are imaged onto a spatially resolving light detector, for example a CCD camera, so that a light distribution in the form of a light spot is detected for each punctiform marker, the size of which spot is determined by the resolution limit of the optical unit.

In this manner, a large number of individual raw data images are taken, in each of which a different active subset is imaged. In an image evaluation process, the centroid positions of the light distributions which represent the punctiform markers present in the bright state are then determined in each individual raw data image. The centroid positions of the light distributions which are ascertained from the individual raw data images are then collated in an overall representation in the form of an overall image data set. The high-resolution overall image produced by this overall representation reflects the distribution of the markers.

For representative reproduction of the sample structure which is to be imaged, a sufficiently large number of marker signals has to be detected. However, since the number of evaluable markers in the respectively active subset is limited, a very large number of individual raw data images have to be taken in order to image the sample structure in its entirety. Typically, the number of individual raw data images is in a range of several tens of thousands, this range varying greatly, since far more images have to be taken for complex structures than for simpler structures in order to be able to resolve the structures.

In addition to the lateral determination of the position of the markers in the object plane (also referred to below as x-y-plane) which is described above, a determination of the position in the axial direction (also referred to below as z-direction) may also take place. "Axial direction" in this case means the direction along the optical axis of the imaging optical unit, i.e. the main direction of propagation of the light.

Three-dimensional localizations are known from what are called "particle-tracking" experiments, as are described in Kajo et al., 1994, Biophysical Journal, 67, Holtzer et al., 2007, Applied Physics Letters, 90 and Toprak et al., 2007, Nano Letters, 7(7). Said localizations have also already been used in image-generating methods which are based on the switching and localization of individual molecules which has been described above. In this regard, reference is made to Huang et al, 2008, Science, 319 and Juette et al., 2008, Nature Methods. With regard to the prior art, reference is further made to Pavani et al., 2009, PNAS, 106.

A punctiform object can be localized in the z-direction in principle in that the change of a light spot detected on the detection surface of the camera is evaluated, this change becoming visible if the point object moves out of the plane of sharpness or focal plane which is optically conjugate with the detection surface. In this case, a point object is to be understood in what follows to mean an object, the dimensions of which are smaller than the diffraction-dependent resolution limit of the imaging optical unit, in particular of the detection objective. In this case, the detection objective images such an object in the form of a three-dimensional focus light distribution in the image space. The focus light distribution generates a light spot on the detection surface of the camera, which spot is portrayed by what is known as the "point-spread function", or PSF for short. If the point object is now moved in the z-direction through the focus, i.e. perpendicularly to the plane of sharpness, the size and shape of the PSF change. If the detection signal which corresponds to the detected light spot is analyzed with regard to the size and shape of the PSF, the actual z-position of the object can be concluded therefrom.

If the point object is located too far away from the plane of sharpness, the light spot generated on the detection surface of the camera is so fuzzy that the corresponding measuring signal is no longer perceptible within the usual measurement noise. Therefore, in the object space, there is a region in the z-direction around the central focal plane or plane of sharpness within which a point object generates a light spot on the detection surface which is still sharp enough to be able to be evaluated in order to localize the point object in the z-direction. This region in the z-direction containing the plane of sharpness is referred to below as "depth of field range".

In the case of three-dimensional localization, there is however the fundamental problem that the PSF originating from a point object is symmetrical with respect to the detection surface. This means that although the PSF changes if the point object is moved out of the plane of sharpness, so that the distance of the point object from the plane of sharpness can be determined, the change in the PSF is symmetrical on both sides of the plane of sharpness, so that it is not possible to decide on which side of the plane of sharpness the point object is located within the depth of field range.

Various methods are known for resolving the problem discussed above. Examples are methods which are referred to among experts as the "astigmatism method" (the above-mentioned documents Kajo et al., Holtzer et al. and Huang et al.), "biplane method" (cf. Toprak et al. and Juette et al.) and "double helix method" (cf. Pavani et al.). What these methods have in common is that, in order to localize the point object in the z-direction, the light spot generated on a detector is analyzed in order to determine a parameter, and a z-position of the point object is associated with this parameter. This association takes place using association information determined in advance which relates the parameter to the z-position of the point object. As a parameter, for example as in the astigmatism method, a quantity is considered which portrays the shape of the light spot, or, as in the case of the biplane method, a quantity is considered which relates the extensions of two light spots to one another, which extensions originate from the same light spot and are generated on detection surfaces the associated planes of sharpness of which are offset from each other in the z-direction in the object space.

In localization microscopy, in which resolutions of far below 100 nm, sometimes even into the region of a few nm, are achieved, optical imaging errors, which inevitably occur in every imaging optical unit, now constitute a considerable problem. Whereas in conventional, diffraction-limited microscopy, in which resolutions, measured in the object space, approximately in the region of 250 nm are obtained, the imaging errors can be sufficiently minimized by precision lens manufacture or additional corrective elements, this has hitherto not been readily possible in localization microscopy. In this case, the resolution is so high that the remaining imaging errors are of considerable relevance. Examples of such imaging errors are chromatic aberrations, spherical aberrations or lateral field distortions, i.e. imaging errors which lead to distortion of the PSF in a plane perpendicular to the optical axis. One example of a lateral field distortion is the coma.

SUMMARY

In an embodiment, the present invention provides a light-microscopic method of localization microscopy for localizing point objects in a sample disposed in an object space. The method includes imaging, by an imaging optical unit having a depth of field range of predetermined axial z-extension along its optical axis in the object space, the sample onto a detector; localizing the point objects in the sample within the depth of field range in that, on the basis of a sample image generated by imaging the sample onto the detector, lateral x/y-positions of the point objects in a direction perpendicular to the optical axis are ascertained; displacing, in the object space relative to the sample, the depth of field range within which the point objects are localized along the optical axis at least once by a predetermined axial z-travel distance which is smaller than the axial-extension of the depth of field range; imaging, by the imaging optical unit in the event of an axially displaced depth of field range, the sample anew onto the detector to generate at least one further sample image; ascertaining the lateral x/y-positions of the point objects anew on the basis of the at least one further sample image; ascertaining lateral x/y-position deviations between the lateral x/y-positions of the same point objects in the sample image and the at least one further sample image; and generating correction information as a function of the lateral x/y-position deviations ascertained, using which information the lateral x/y-positions of the point objects which have been ascertained on the basis of at least one of the further sample images are corrected.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

An embodiment of the invention provides a light-microscopic method for localizing point objects, such that lateral field distortions are reliably corrected with reduced technical complexity.

In an embodiment, the depth of field range within which the point objects are localized is displaced in the object space relative to the sample along the optical axis at least once by a predetermined axial z-travel distance which is smaller than the axial extension of the depth of field range, and, in the event of an axially displaced depth of field range, the sample is imaged anew onto the detector by means of the imaging optical unit and a further sample image is generated; the lateral x/y-positions of the point objects are ascertained anew on the basis of this further sample image; lateral x/y-position deviations between the lateral x/y-positions of the same point objects in each case ascertained on the basis of the various sample images are ascertained; and correction information is generated as a function of the lateral x/y-position deviations ascertained, on the basis of which information the lateral x/y-positions of the point objects which have been ascertained on the basis of at least one of the various sample images are corrected.

Unlike conventional solutions, in which an attempt is made to correct the imaging errors solely by apparatus-related measures, in particular by manufacturing the optical elements used in the imaging optical unit in a manner which is as error-free as possible, an embodiment of the invention goes down a route in which correction of the imaging errors results from the analysis of the localized positions themselves. Also, no additional calibration or any measurement provided specifically for determining optical errors is required, as a result of which the technical complexity is considerably reduced.

The solution according to an embodiment of the invention provides for displacement of the depth of field range along the optical axis of the imaging optical unit such that there is a certain overlap along the optical axis between the original depth of field range and the displaced depth of field range in the object space. This overlap is achieved in that the axial z-travel distance by which the depth of field range is moved along the optical axis is less than the axial z-extension of the depth of field range. In this case, the z-travel distance lies for example in the range of 5 to 90%, 10 to 80%, 15 to 70%, 20 to 60% or 25 to 50% of the axial z-extension of the depth of field range. It goes without saying that these value ranges are to be understood to be only examples.

The displacement according to an embodiment of the invention of the depth of field range by the axial z-travel distance, which is less than the axial extension of the depth of field range, is therefore to be understood in such a way that the two depth of field ranges considered, namely the original and the displaced depth of field range, have the above-mentioned overlap along the optical axis. This means that an embodiment of the invention also covers a step sequence of displacements in the depth of field range, in which in an individual step the depth of field range is displaced by a travel distance which is greater than the extension of the depth of field range, provided that the step sequence as a whole results in the ultimately desired axial overlap being achieved between the depth of field ranges considered.

An embodiment of the invention provides for taking not only a single sample image of a given three-dimensional structure of point objects, but rather at least one further sample image having a depth of field range which is displaced along the optical axis, so that the same point objects are imaged in various z-positions of the depth of field range.

Owing to the lateral field distortion which is to be corrected according to an embodiment of the invention, in the two sample images, the point objects mentioned have position deviations in their lateral x/y-positions as a function of their respective z-positions. From these lateral x/y-position deviations, correction information which is a measurement of the lateral field distortion can now be generated. This correction information can then be used to correct the lateral x/y-positions of the point objects which have the imaging error.

As has already been mentioned at the outset, the depth of field range according to an embodiment of the invention in the object space is to be understood to mean a region in the z-direction around the central focal plane or plane of sharpness within which a point object generates a light spot on the detector which is still sharp enough to be able to be evaluated in order to localize the point object. In this case it is not necessary to exhaust this maximum possible depth of field range completely. Thus it may be useful, depending on the desired localization accuracy, to deliberately reduce the depth of field range and to thus exclude from the evaluation light spots which are already very fuzzy, but which can still be evaluated per se. The light spots generated on the detector do not necessarily have to be strictly spatially separated from one another in order to determine the lateral x/y-positions. Overlapping light distributions can also be analyzed, to the extent that the positions of the point objects can be determined, by means of suitable algorithmic methods, as are known from the literature for example as multi-fit methods or maximum-likelihood methods.

The method according to an embodiment of the invention is not only suitable for correcting those imaging errors which are caused by the optical elements of the imaging optical unit. Rather, an embodiment of the invention also makes it possible to correct optical faults which are caused by the sample itself. Such optical faults are frequently dependent on the location at which they occur in the sample, or on the ambient temperature. They can thus be controlled only with difficulty using conventional methods, in which for example optical corrective elements are suitably triggered in a technically very complex manner. This applies all the more so since these conventional methods as a rule provide for an iterative correction of the imaging errors, in which the sample is repeatedly photographed and therefore must not change. In contrast, in localization microscopy the signal detected by the detector changes constantly due to the flashing individual molecules, so that as a rule no sample image is exactly identical to another.

The lateral x/y-position of a point object is to be understood in the following to mean a position which, for example with reference to a Cartesian coordinate system in which the z-axis lies parallel to the optical axis of the imaging optical unit, is measured in the direction of the x-axis and/or in the direction of the y-axis, the x-axis and the y-axis being arranged perpendicularly to the y-axis.

Preferably at least one reference plane lying perpendicularly to the optical axis is defined within the depth of field range, which plane remains stationary relative to the depth of field range when the depth of field range is displaced. One of the sample images in this case is set as a reference image, a comparison structure which represents at least one of those point objects which are arranged in the reference plane of the depth of field range when photographing the reference image being defined on the basis of this reference image. The comparison structure is then identified in the at least one other sample image. On the basis of the various sample images, the lateral x/y-position of the comparison structure is ascertained in each case. Then, the lateral x/y-position deviation between the lateral x/y-positions of the reference structure which are ascertained on the basis of the various sample images is determined. Finally, the correction information is generated as a function of the lateral x/y-position deviation ascertained for the comparison structure.

The reference plane is for example the central focal plane or plane of sharpness within the depth of field range. Said plane is moved along the optical axis, displacing the depth of field range, and thus scans the object space, as it were. Using one of the sample images which is set as a reference image, a comparison structure is defined which is also present in the other sample images, but in different z-positions there and consequently—due to the lateral field distortion—also in other x/y-positions within the associated depth of field range. With the aid of the comparison structure, the lateral x/y-position deviations can thus be ascertained reliably as a function of the z-position.

Preferably, the depth of field range is axially displaced in a plurality of steps. In each of these steps, the lateral x/y-position deviation of the comparison structure which is ascertained on the basis of the associated sample image is ascertained relative to the lateral x/y-position of the comparison structure which is ascertained on the basis of the reference image. An association function is generated as correction information, the function values of which in each case indicate the lateral x/y-position deviation of the associated comparison structure ascertained in the respective step, depending on the axial z-position thereof along the optical axis. The association function constitutes a correction prescription which, as a function of the distance of a point object from the reference plane, provides for a correction of the lateral x/y-position which exactly compensates for the erroneous localization of this point object resulting from the lateral field distortion.

Values of the association function which lie between the function values ascertained by the step-wise displacement of the depth of field range can be determined for example by interpolation. In this manner, a constant association function can be ascertained, although only a few discretely ascertained function values are available due to the step-wise displacement of the depth of field range.

In one possible embodiment, the lateral x/y-positions of the point objects are corrected by image processing directly in the associated sample image. This has the advantage that the corrected positions of the point objects are directly displayed to the user without having to take the roundabout route of correction of previously stored positions and a sample image newly generated on the basis of the corrected positions.

Preferably, the comparison structure in the at least one other sample image is identified as a function of the image brightness detected on the detector, i.e. taking into account the total number of light spots generated on the detector which contribute to this structure. This embodiment is advantageous in particular when the x/y-positions ascertained when the depth of field range is displaced are used not only to correct positions previously having imaging errors, but at the same time are used to generate a high-resolution overall localization image. As a result, disturbing differences in brightness in the overall localization image can be avoided.

The sum of the individual axial z-travel distances is substantially identical to the axial z-extension of the depth of field range. It is, however, likewise possible to adjust the depth of field range in the z-direction as a whole by a distance which is greater than the extension of the depth of field range. If in this case the sample images generated in individual steps are combined to form an overall localization image once the positions of the point objects have been corrected, this covers a range in the z-direction which is greater than the depth of field range. Thus in particular complex three-dimensional structures can be imaged at high resolution.

Preferably, the axial z-travel distance is detected by means of a sensor. This ensures that the axial z-travel distance, which is included in the correction of the lateral x/y-positions of the point objects, is always precisely known.

The depth of field range can be displaced relative to the sample in that either the sample is moved along the optical axis relative to the imaging optical unit or alternatively the imaging optical unit is moved along the optical axis relative to the sample. The invention is, however, not restricted to this. Thus, it is for example likewise possible to use a deformable lens, a deformable mirror, a spatial light modulator or the like in order to displace the depth of field range in the object space along the optical axis of the imaging optical unit. In principle, it is possible to displace the depth of field range in any desired manner.

In a particularly preferred embodiment, the z-position of the respective point object along the optical axis is ascertained in that a parameter of a light spot which represents the point object in the respective sample image is ascertained and the z-position is associated with this parameter using predetermined association information. For example, a quantity is considered as the parameter which, as in the astigmatism method mentioned at the outset, portrays the shape of the light spot which represents the point object. Alternatively, a parameter can also be used which, as in the case of the known biplane method, relates the extensions of two light spots to one another, which extensions originate from the same light spot and are generated on detection surfaces, the associated planes of sharpness of which are offset from each other in the z-direction in the object space.

Preferably, the z-positions of the point objects ascertained in the sample image are compared with the z-positions of the same point objects ascertained in the further sample image as a function of the predetermined axial z-travel distance. On the basis of this comparison, z-correction information is then generated, using which the z-positions of the point objects which are ascertained as a function of the association information are corrected. This configuration avoids the problem that the association information determined in advance of the light-microscopic measurement proper, which information permits an association between the parameter ascertained in the measurement and the axial z-position of the point object, is frequently so inaccurate that precise determination of the z-position is difficult. In this case the association information (which is inaccurate from the outset) can be corrected using the z-correction information.

According to an embodiment of the invention, a light-microscopic apparatus for localizing point objects is provided.

Figure 1:
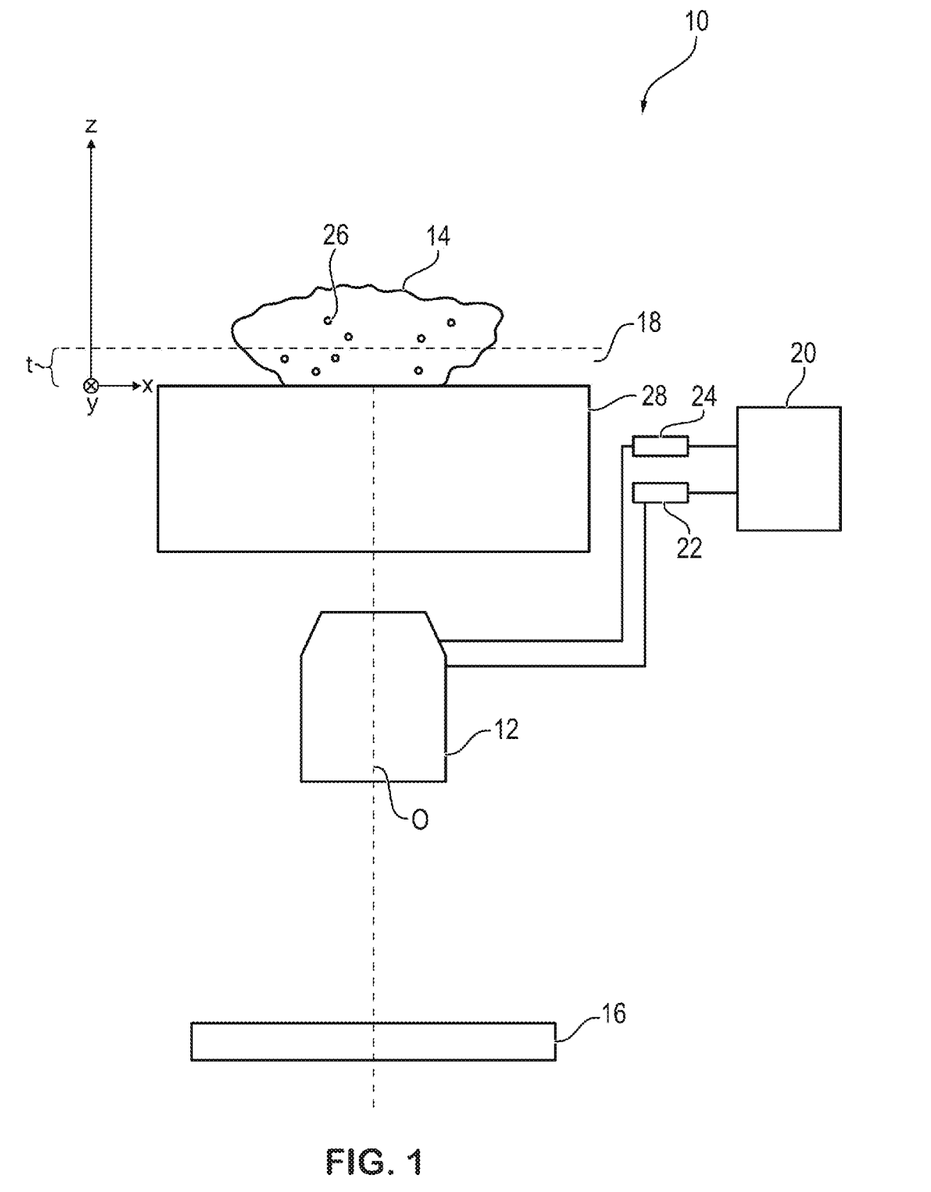
FIG. 1 is a schematic view of a light-microscopic apparatus according to an embodiment of the invention.

FIG. 1 is a purely schematic view of a light-microscopic apparatus 10 comprising an imaging optical unit 12 which forms an image of a sample 14 on a detector 16. The sample 14 is arranged on a sample holder 28.

The imaging optical unit 12 has a depth of field range 18 which has an axial extension t along an optical axis O. In the following, it is to be assumed that the optical axis O lies parallel to an axis z of a Cartesian coordinate system, the further axes x and y of which are arranged perpendicularly to the optical axis O.

The apparatus 10 further comprises a control unit 20 which controls the overall operation of the apparatus 10. In particular, the control unit 20 has calculation means which carry out the calculations and evaluations necessary for localization. The control unit 80 furthermore controls a piezo actuator 22, by means of which the imaging optical unit 12 can be moved along the optical axis O in order to displace the depth of field range 78 along the optical axis O, i.e. in the z-direction. A sensor 24 coupled to the control unit 20 detects the z-travel distance by which the imaging optical unit 12, and thus the depth of field range, are displaced within the object space.

The sample 14 contains a plurality of point objects 26 which are formed by fluorescent markers which adhere to the structures to be imaged. During the microscope photography, the point objects 26 are imaged individually onto the detector 16 as light spots. The light spots thus generated are evaluated in the control unit 20 in order to localize the point objects 26.

The apparatus 10 of FIG. 1 serves to localize the point objects 26 contained in the sample 14 in the object space 28. To do this, the control unit 20 of the apparatus 10 ascertains both the z-position of the respective point object along the optical axis O and the lateral x/y-position in a plane perpendicular to the optical axis O.

It is explained below how a lateral field distortion, such as is caused for example by a coma, is corrected according to an embodiment of the invention.

Figure 2:
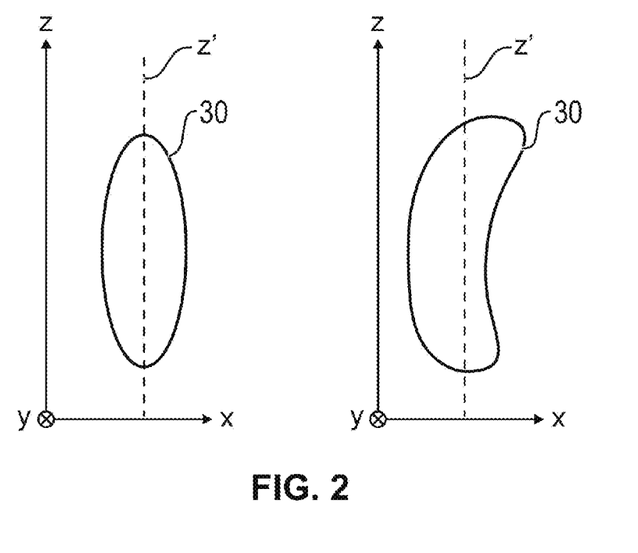
FIG. 2 depicts two schematic sectional views, one of which is a view of a distortion-free PSF and the other of which is a view of a PSF distorted by coma in the object space.
Figure 3:
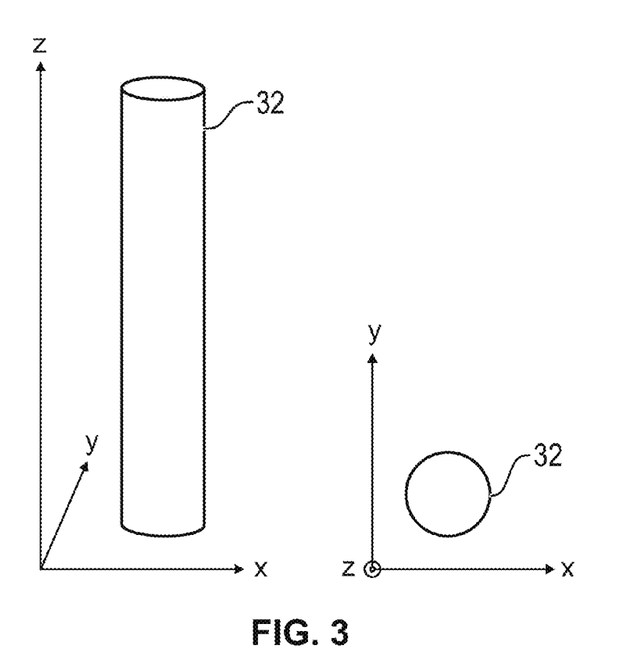
FIG. 3 depicts two schematic views which show a three-dimensional, tube-like structure without coma.
Figure 4:
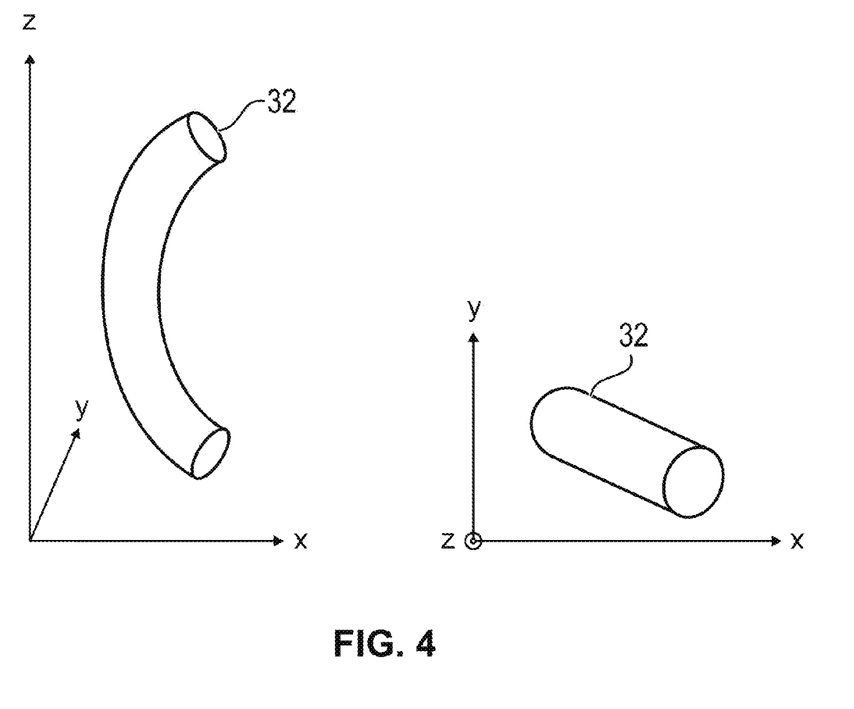
FIG. 4 depicts two schematic views corresponding to FIG. 3 which show the tube-like structure with coma.

In this case, first of all with reference to FIGS. 2 to 4 it is illustrated how a lateral image distortion affects the accuracy with which point objects 26 are localized in the lateral direction.

FIG. 2 shows how the coma leads to a distortion of the PSF associated with the respective point object in the three-dimensional space. In this case, the left-hand partial image of FIG. 2 first of all illustrates the ideal case of an error-free PSF 30, which is radially symmetrical along its longitudinal axis, designated z' in FIG. 2. The longitudinal axis z' of the PSF 30 should in this case be parallel to the optical axis O and therefore to the z-axis of the coordinate system illustrated in FIG. 2.

The coma now results in a distortion of the PSF 30, which breaks the radial symmetry of the PSF 30, as is illustrated in the right-hand partial image of FIG. 2. This breaking of the radial symmetry results in a lateral displacement of the centroid of the PSF 30 in the x-y-plane. As can be directly inferred from FIG. 2, the lateral displacement of the centroid is dependent on the z-position.

The coma therefore results in the centroids of the PSFs associated with the individual point objects no longer being in the same x/y-position at various z-positions. A corresponding effect is obtained if tilting of the PSF in space is considered instead of the coma.

Therefore, if there are now imaging errors which result in the above-mentioned effect of displacement of the centroid, this leads to image errors in the high-resolution sample image, as a comparison of FIGS. 3 and 4 shows. In this case, FIG. 3 shows the image of a three-dimensional, tube-like structure 32 which extends along the z-axis. The structure 32 is intended to be dyed for example using a suitable dye, the molecules of which are localized in the manner explained at the outset. A high-resolution image is then composed from the position information which is ascertained and stored. This is illustrated in the right-hand partial image of FIG. 3 for a two-dimensional projection, provided by way of example, of all the point objects localized in the three-dimensional space. In this two-dimensional projection, the structure considered is represented by a circle.

While FIG. 3 shows the error-free case, FIG. 4 illustrates the effect of a lateral field distortion. Accordingly, the lateral field distortion leads to molecule positions which are located in different z-positions but are, in themselves, in the same x/y-position, are wrongly placed at various x/y-positions, as the left-hand partial image of FIG. 4 shows. Thus, in the two-dimensional projection, a deviation from the original circular shape can be seen, as the right-hand partial image of FIG. 4 shows.

With reference to FIGS. 5 to 12, it is explained by way of example below how the lateral image field distortion described above is corrected according to an embodiment of the invention.

Figure 5:
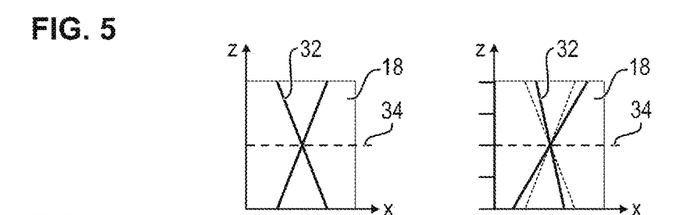
FIG. 5 is a schematic view showing an X-shaped structure together with a depth of field range and the image thereof.

FIG. 5 shows, in the left-hand part of the figure, an X-shaped structure 32, which by way of example extends in the x-z-plane. The X-shaped structure 32 is intended to be dyed using a suitable dye, which form the point objects 26 to be localized (cf. FIG. 1). In order to localize these dyes, the positions thereof within the depth of field range 18 illustrated in FIG. 5 as a rectangular surface are ascertained. The resultant high-resolution image is illustrated in the right-hand part of FIG. 5. Thus, the right-hand part of the figure shows the image space which is optically conjugate with the object space illustrated in the left-hand part of the figure.

Below, it is assumed for simplicity that the imaging optical unit 12 causes a field distortion solely in the x-direction. The resultant image, which is distorted in the x-direction, is illustrated by unbroken lines. In contrast, the image which would be produced in the case of ideal imaging without any field distortion is shown in broken lines.

In FIG. 5, in addition the central plane of sharpness or focal plane of the depth of field range 18 is designated 34. In this case it should be pointed out that the same reference numerals are given both in the left-hand and in the right-hand part of FIG. 5 (and also in the further FIGS. 5 to 10), although the left-hand part of the figure represents the object space and the right-hand part of the figure the image space which is optically conjugate therewith.

FIGS. 6 to 10 show how the depth of field range 18 is displaced along the optical axis O in a plurality of steps in each case by a z-travel distance Δz in the object space in order to carry out the correction according to an embodiment of the invention of the lateral x/y-positions of the point objects 26.

The method illustrated in FIGS. 6 to 10 is based on the following consideration. As a result of the lateral field distortion in the x-direction, point objects which, although lying in the same x-position, are in different z-positions within the depth of field range 18, are illustrated in different x-positions in the image generated by the imaging optical unit 12. However, it is possible to define a z-position within the depth of field range 18 in which the x-position allocation between the object space and image space is by definition correct. This z-position within the depth of field range 34 thus forms a reference position. The x-y-plane which is located in the object space at this z-position accordingly defines a reference plane. In the present embodiment, the central plane of sharpness 34 of the depth of field range 18 is used as such a reference plane. The step sequence shown in FIGS. 6 to 10 now has the aim of generating an association function as correction information which, as a function of the distance of a point object from the reference plane 34, provides for a correction of the x-position which exactly compensates for the erroneous localization in the x-direction resulting from the lateral field distortion.

The association function in the present embodiment is generated in that not only one image of the X-shaped structure 32 but a total of five images each having a depth of field range 18 displaced by $\Delta z$ are generated.

Figure 6:
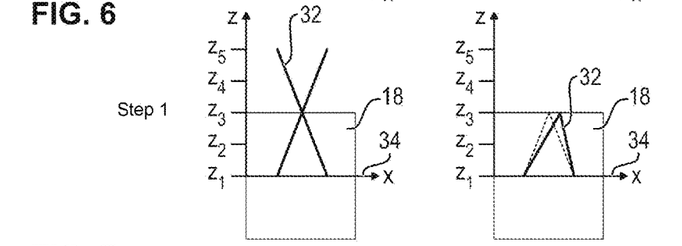
FIG. 6 is a schematic view showing the X-shaped structure and the image thereof in a first step of a method according to an embodiment of the invention given by way of example.

The correction method given by way of example begins in step 1 according to FIG. 6, in which the plane of sharpness 34 of the depth of field range 18 which acts as a reference plane is located within the object space along the optical axis O in the position z1. The right-hand part of FIG. 6 shows the high-resolution image resulting from this arrangement.

Figure 7:
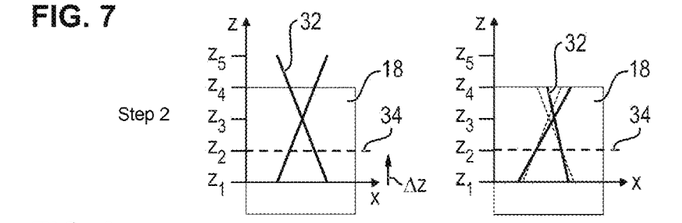
FIG. 7 is a schematic view showing the X-shaped structure and the image thereof in a second step of the method according to an embodiment of the invention.

Then, in step 2 according to FIG. 7, the imaging optical unit 12 and therefore the depth of field range 18 thereof is displaced along the optical axis by the known z-travel distance $\Delta z$ ($=z_2-z_1$), so that the plane of sharpness 34 serving as a reference plane arrives in the position z2. Again in this arrangement a high-resolution image is generated, the positions localize in the z-direction being correspondingly corrected by the amount $\Delta z$ in order not to displace the resulting image by $\Delta z$ compared with the image generated in the preceding step 1. In the image thus generated, the X-shaped structure 32 is illustrated such that it is distorted in the z-direction for all the z-positions apart from z2, as can again be seen from the ideal structure illustrated in broken lines. As a comparison of FIGS. 6 and 7 shows, the distortion in the high-resolution image changes with the displacement of the depth of field range 18, since the X-shaped structure changes its position within the depth of field range 34.

Figure 8:
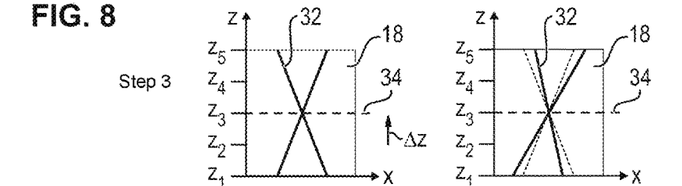
FIG. 8 is a schematic view showing the X-shaped structure and the image thereof in a third step of the method according to an embodiment of the invention.
Figure 9:
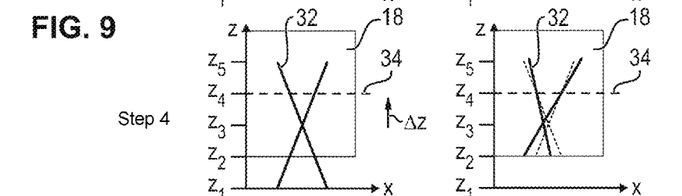
FIG. 9 is a schematic view showing the X-shaped structure and the image thereof in a fourth step of the method according to an embodiment of the invention.
Figure 10:
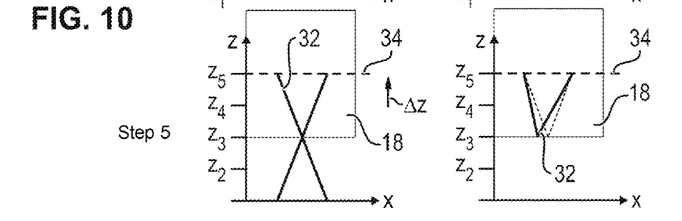
FIG. 10 is a schematic view showing the X-shaped structure and the image thereof in a fifth step of the method according to an embodiment of the invention.
Figure 11:
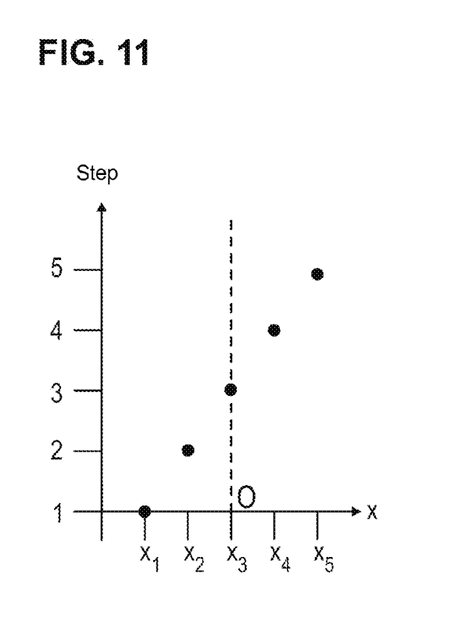
FIG. 11 is a graph showing lateral x-positions of a comparison structure in the steps illustrated in FIGS. 6 to 10.
Figure 12:
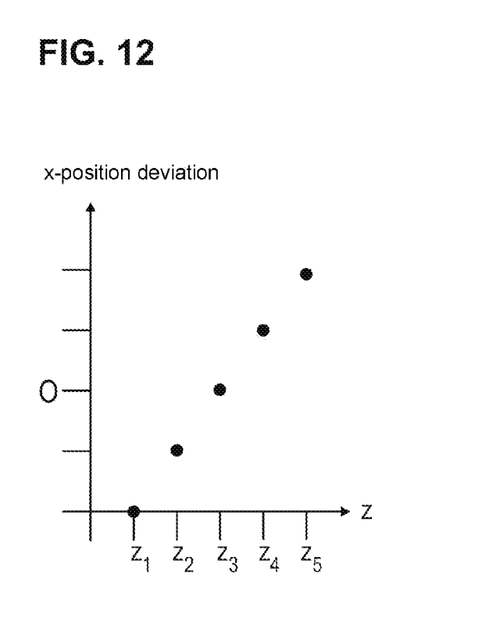
FIG. 12 is a graph showing an association function according to an embodiment of the invention, the function values of which indicate lateral x-position deviations as a function of the z-position.

As shown in FIGS. 8 to 10, in further steps 3, 4 and 5 the depth of field range 18 is then displaced along the optical axis O successively in each case by the predetermined z-travel distance $\Delta z$. As a result, the reference plane 34 as it were scans the X-shaped structure 32 in the object space along the optical axis O.

Once the five high-resolution images have been generated, for example that part of the X-shaped structure 32 which is located in the reference plane 34 in step 3 is selected as comparison structure. This comparison structure is then also identified in the other images generated in steps 1, 2, 4 and 5. Then, the lateral x-position of the comparison structure is ascertained on the basis of the individual images generated in the various steps. Since the comparison structure has been in various z-positions relative to the depth of field range 18 when the individual images have been taken, the x-positions differ from image to image as a result of the field distortion in the x-direction. These are illustrated in the graph according to FIG. 11 for the individual steps 1 to 5.

The desired association function is finally obtained by plotting the lateral x-position deviations of the comparison structure ascertained in steps 1, 2, 4 and 5 relative to the x-position of the comparison structure ascertained in step 3 against the associated z-positions. This is illustrated in the graph according to FIG. 12. The five function values of the association function which are associated with steps 1 to 5 can then be used as intermediate points in order, for example by way of interpolation, to generate intermediate values, in order to finally obtain a constant association function. Using such an association function, the lateral position deviations for all the z-positions can be indicated in order to generate a distortion-free, high-resolution image.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

LIST OF REFERENCE NUMERALS 10 light-microscopic apparatus
12 imaging optical unit
14 sample
16 detector
18 depth of field range
20 control unit
22 adjusting unit
24 sensor
26 point objects
28 sample holder
30 PSF
32 tube-like structure
32 X-shaped structure
34 reference plane

The invention claimed is:
1. A light-microscopic method of localization microscopy for localizing point objects in a sample disposed in an object space, the method comprising:
imaging, by an imaging optical unit having a depth of field range of predetermined axial z-extension along its optical axis in the object space, the sample onto a detector;
localizing the point objects in the sample within the depth of field range on the basis of a sample image generated by imaging the sample onto the detector to determine lateral x/y-positions of the point objects in a direction perpendicular to the optical axis;
displacing, in the object space relative to the sample, the depth of field range within which the point objects are localized along the optical axis at least once by a predetermined axial z-travel distance which is smaller than the axial z-extension of the depth of field range;

imaging, by the imaging optical unit in the event of an axially displaced depth of field range, the sample anew onto the detector to generate at least one further sample image;

ascertaining the lateral x/y-positions of the point objects anew on the basis of the at least one further sample image;

ascertaining lateral x/y-position deviations between the lateral x/y-positions of the same point objects in the sample image and the at least one further sample image; and using the ascertained lateral x/y-position deviations to generate correction information which, as a function of a distance of the point objects from a reference plane within the depth of field range, corrects lateral field distortion.

2. The light-microscopic method according to claim 1, wherein the reference plane lies perpendicularly to the optical axis and remains stationary relative to the depth of field range when the depth of field range is displaced;

wherein one of the sample images is set as a reference image and a comparison structure which represents at least one of the point objects arranged in the reference plane of the depth of field range when taking the reference image is defined on the basis of the reference image;

wherein the comparison structure is identified in the at least one other sample image;

wherein on the basis of the various sample images, the lateral x/y-position of the comparison structure is ascertained in each case;

wherein the lateral x/y-position deviation between the lateral x/y-positions of the comparison structure which are ascertained on the basis of the various sample images is determined; and wherein the correction information is generated as a function of the lateral x/y-position deviation ascertained for the comparison structure.

3. The light-microscopic method according to claim 2, wherein the depth of field range is axially displaced in a plurality of steps, wherein in each of these steps, the lateral x/y-position deviation of the comparison structure ascertained on the basis of the associated sample image is ascertained relative to the lateral x/y-position of the comparison structure ascertained on the basis of the reference image, and wherein an association function is generated as correction information, the function values of which in each case indicate the lateral x/y-position deviation of the associated comparison structure ascertained in the respective step, depending on the axial z-position thereof along the optical axis.

4. The light-microscopic method according to claim 3, wherein values of the association function which lie between the function values ascertained by step-wise displacement of the depth of field range are determined by interpolation.

5. The light-microscopic method according to claim 3, wherein the lateral x/y-positions of the point objects are corrected by image processing directly in the associated sample image.

6. The light-microscopic method according to claim 3, wherein the lateral x/y-positions of the point objects are corrected in a data set obtained from the associated sample image, and wherein a corrected sample image is generated on the basis of the corrected data set.

7. The light-microscopic method according to claim 2, wherein the comparison structure in the at least one other sample image is identified as a function of image brightness detected on the detector.

8. The light-microscopic method according to claim 1, wherein the lateral x/y-position deviations are ascertained using a correlation method.

9. The light-microscopic method according to claim 1, wherein the sum of the individual axial z-travel distances is substantially identical to the axial z-extension of the depth of field range.

10. The light-microscopic method according to claim 1, wherein the axial z-travel distance is detected by a sensor.

11. The light-microscopic method according to claim 1, wherein the depth of field range is displaced in the object space relative to the sample along the optical axis by the axial z-travel distance, in that the sample is displaced along the optical axis relative to the imaging optical unit or in that the imaging optical unit is displaced along the optical axis relative to the sample.

12. The light-microscopic method according to claim 1, wherein the z-position of a respective point object along the optical axis is ascertained in that a parameter of a light spot which represents the respective point object in the sample image is ascertained and the z-position is associated with the parameter using predetermined association information.

13. The light-microscopic method according to claim 12, wherein the z-positions of the point objects ascertained in the sample image are compared with the z-positions of the same point objects ascertained in the further sample image as a function of the predetermined axial z-travel distance; and wherein z-correction information is generated as a function of this comparison using which the z-positions of the point objects which are ascertained as a function of the association information are corrected.

14. A light-microscopic apparatus for localizing point objects in a sample, the apparatus comprising:

an imaging optical unit having, in an object space and along its optical axis, a depth of field range of predetermined axial z-extension;

a detector onto which the imaging optical unit is operable to image a sample disposed in the object space;

a controller operable to localize point objects contained in the sample within the depth of field range to ascertain, on the basis of a sample image which the imaging optical unit generates on the detector, lateral x/y-positions of the point objects in a direction perpendicular to the optical axis; and an adjustment unit, triggered by the control unit, operable to displace the depth of field range, within which the point objects are localized, in the object space relative to the sample along the optical axis at least once by a predetermined axial z-travel distance which is smaller than the axial extension of the depth of field range;

wherein, in the event of an axially displaced depth of field range, the imaging optical unit is operable to image the sample anew onto the detector and generate a further sample image;

wherein the control unit is operable to ascertain the lateral x/y-positions of the point objects anew on the basis of the further sample image;

wherein the control unit is operable to ascertain lateral x/y-position deviations between the lateral x/y-positions of the same point objects in each case ascertained on the basis of the sample images; and wherein the control unit is operable to use the ascertained later x/y-position deviations to generate correction information which, as a function of a distance of the point objects from a reference plane within the depth of field range, corrects lateral field distortion.

15. The method according to claim 1, wherein an adjustment unit and a sensor are used to ensure that the depth of field range is displaced by the predetermined axial z-travel distance between taking the sample images.

16. The light-microscopic apparatus according to claim 14, further comprising a sensor operable to detect the axial z-travel distance of the depth of field range.

* * * * *